(12) United States Patent
Owen et al.

(10) Patent No.: US 9,719,950 B2
(45) Date of Patent: Aug. 1, 2017

(54) SAMPLE-SPECIFIC REFERENCE SPECTRA LIBRARY

(71) Applicant: FEI Company, Hillsboro, OR (US)

(72) Inventors: Michael James Owen, Geebung (AU); Ashley Donaldson, Gordon Park (AU); Garth Howell, McDowall (AU); Phillip John Christopher Parker, Corinda (AU)

(73) Assignee: FEI Company, Hillsboro, OR (US)

( * ) Notice: Subject to any disclaimer, the term of this patent is extended or adjusted under 35 U.S.C. 154(b) by 213 days.

(21) Appl. No.: 14/630,704

(22) Filed: Feb. 25, 2015

(65) Prior Publication Data

US 2016/0245762 A1    Aug. 25, 2016

(51) Int. Cl.
*G01N 23/225* (2006.01)
*H01J 37/252* (2006.01)
*H01J 37/244* (2006.01)
*G01J 3/44* (2006.01)

(52) U.S. Cl.
CPC ............ *G01N 23/2252* (2013.01); *G01J 3/44* (2013.01); *H01J 37/244* (2013.01); *H01J 37/252* (2013.01)

(58) Field of Classification Search
USPC ........................................ 250/307, 306, 310
See application file for complete search history.

(56) References Cited

U.S. PATENT DOCUMENTS

| 6,326,619 | B1 | 12/2001 | Michael et al. |
| 6,835,931 | B2 * | 12/2004 | Wright ................. G01N 23/203 250/307 |
| 8,653,457 | B2 | 2/2014 | Stoks |
| 8,880,356 | B2 | 11/2014 | Corbett et al. |
| 8,937,282 | B2 | 1/2015 | Owen et al. |
| 9,048,067 | B2 | 6/2015 | Owen |
| 9,091,635 | B2 | 7/2015 | Owen |
| 2014/0032131 | A1 | 1/2014 | Owen |
| 2014/0117231 | A1 | 5/2014 | Owen et al. |
| 2014/0183357 | A1 | 7/2014 | Smith et al. |
| 2015/0122992 | A1 | 5/2015 | Owen et al. |

* cited by examiner

*Primary Examiner* — Kiet T Nguyen
(74) *Attorney, Agent, or Firm* — Scheinberg & Associates, P.C.; Michael O. Scheinberg

(57) ABSTRACT

A method and apparatus are provided for identifying a material with a sample-specific reference spectral list or library. A sequential approach to SEM-EDS automated mineralogy classification is carried out by performing two or more material classification analyses. A pre-classification step restricts the processing of spectra deconvolution algorithms to a subset of spectra that pass a dominant mineral criteria resulting in a significantly reduced subset of reference spectra that occur within the measured sample in pure enough form at a given minimum quantity. The following complex classification stages involving deconvolution of multiple constituents within measured spectra is based on this sample relevant subset.

21 Claims, 10 Drawing Sheets

| Simulant | Before | After |
|---|---|---|
| 101-graphite-calcite | 93.35 | 94.27 |
| 104-graphite-calcite | 74.64 | 75.16 |
| 105-graphite-calcite-kaolinite | 70.77 | 71.9 |
| 106-graphite-calcite-kaolinite | 71.08 | 72.47 |
| 107-quartz-kaolinite | 64.04 | 64.52 |
| 108-graphite-kaolinite | 65.58 | 66.11 |
| 109-orthoclase-illite | 52.26 | 56.31 |
| 111-muscovite-illite | 46.2 | 55.4 |
| 113-rectorite-illite-montmorillinite | 31.75 | 53.71 |
| 115-illite-montmorillonite | 14.22 | 24.57 |
| 117-dolomite-clinochlore | 12.57 | 9.79 |
| 118-calcite-dolomite | 64.83 | 86.1 |
| 119-feo-dolomite-calcite | 47.33 | 43.69 |
| 120-calcite-gypsum | 85.12 | 85.35 |
| 121-apatite-gypsum | 83.58 | 83.16 |
| 122-hematite-carbon | 89.22 | 98.3 |
| OLD_01-BHX820 | 47.08 | 49.55 |
| OLD_04-PRC01-OC | 90.96 | 93.82 |
| OLD_05-PRC01-HC | 91.74 | 92.45 |
| OLD_06-PRC01-LC | 91.29 | 91.8 |
| OLD_07-PRC12-OC | 68.19 | 67.47 |
| OLD_08-PRC12-HC | 68.37 | 70.32 |
| OLD_09-PRC12-LC | 72.97 | 74.83 |
| OLD_10-SMR-OC | 59.63 | 60.25 |
| OLD_11-SMR-HC | 58.31 | 62.8 |
| OLD_12-NDFH-OC | 54.56 | 60.37 |
| OLD_13-NDFH-HC | 54.14 | 58.45 |
| OLD_14-NDFH-LC | 51.52 | 54.9 |
| OLD_ALS1-Quartz50-Dolomite30-Pyrite20 | 68.03 | 74.17 |
| Average | 63.56310345 | 67.31 |

FIG. 5

| Sample | Before | After |
|---|---:|---:|
| VacaMuerta_01 | 88.07 | 91.72 |
| VacaMuerta_02 | 90.29 | 92.04 |
| VacaMuerta_03 | 81.53 | 87.41 |
| VacaMuerta_04 | 83.67 | 89.7 |
| VacaMuerta_05 | 91.32 | 92.59 |
| VacaMuerta_06 | 95.01 | 97.04 |
| VacaMuerta_07 | 91.1 | 95.56 |
| VacaMuerta_08 | 86.06 | 86.57 |
| VacaMuerta_09 | 89.34 | 93.15 |
| VacaMuerta_10 | 86.92 | 90.2 |
| VacaMuerta_11 | 91.31 | 92.2 |
| VacaMuerta_12 | 89.76 | 89.22 |
| VacaMuerta_13 | 89.34 | 95.28 |
| VacaMuerta_14 | 88.15 | 92.81 |
| VacaMuerta_15 | 80.03 | 76.87 |
| VacaMuerta_16 | 78.75 | 86.39 |
| VacaMuerta_17 | 85.13 | 90.16 |
| Average | 87.39882353 | 90.52411765 |

…

SAMPLE-SPECIFIC REFERENCE SPECTRA LIBRARY

TECHNICAL FIELD OF THE INVENTION

The present invention relates generally to methods for identifying minerals combinations of materials at points in a sample.

BACKGROUND OF THE INVENTION

Mineral analysis systems are used to determine the composition of samples. Examples of such mineral analysis systems include the QEMSCAN® (Quantitative Evaluation of Minerals by Scanning electron microscopy) and MLA (Mineral Liberation Analyzer) from FEI Company, Hillsboro, Oreg., the assignee of the present invention.

The sample, typically in the form of small granules fixed in epoxy in a 30 mm diameter sample block, is placed in a vacuum chamber. An electron beam is directed toward a series of dwell points on the sample and, in a process called "energy dispersive x-ray spectroscopy" or "EDS," the energies of x-rays coming from the each point of the sample in response to the electron beam are measured and plotted in a histogram to form a spectrum represented of the composition of that point. As the electron beam is scanned across the sample surface, a spectrum can be collected at each point on the scan. Because the electron beam cannot be deflected sufficiently to scan the entire width of the sample block, the sample block is divided into tiles, with the size of the tiles limited by the maximum deflection of the electron beam. A tile is scanned with the beam being addressed to each dwell point in the tile, and then the sample stage is moved and a subsequent tile is scanned until the entire sample block has been scanned. FIG. 10 shows a sample block 1002 divided into tiles 1004, each tile having multiple dwell points 1006. FIG. 10 is not drawn to scale.

A compositional map of the sample can be compiled, with each scanned point, or dwell point, on the sample corresponding to a pixel on the compositional map. The dwell points on the sample are also sometimes referred to as pixels. Each element produces a unique X-ray spectrum that is characteristic of the element's unique atomic structure. A measured spectrum can be compared to a library of known reference spectra of various elements to determine which elements and minerals are present. The measured spectrum is compared to combinations of known spectra of elements and minerals to determine the composition at each point, as the point can include multiple minerals. Determining the component spectra that make-up of a measured x-ray spectrum composed of multiple materials is referred to as "deconvolution" of the spectrum.

Backscattered electron (BSE) detectors are also used for mineral analysis in conjunction with x-ray detectors. The intensity of the BSE signal is a function of the average atomic number of material under the electron beam, and this relationship can be used in mineral identification.

Determining the mineral phases that are represented by the x-ray spectrum from a point of unknown composition is computationally intensive. A "mineral phase" is used herein includes not only minerals, but also elements in pure form. A typical prior art approach to material classification attempts to match the experimentally obtained x-ray spectrum from each point on a sample with combinations of reference spectra from library of spectra of known minerals. A difference metric is computed to represent the degree of similarity between the measured data and combinations of known spectra. In one approach, the measured spectrum is compared with every possible combination of spectra from a reference list to determine the best match as indicated by the lowest difference metric. Because the reference list can contain a large number of reference spectra, comparing every possible combination of reference spectra requires a substantial processing time.

In some mineral classification algorithms, increasing the number of reference spectra causes a non-linear increase in overall analysis time. Processing times can increase exponentially as the number of spectra in the spectral reference list increases. While processing time can be reduced by limiting the number of reference spectra considered to a subset of the most common minerals, limiting the number of reference spectra can result in an important sample-specific phase remaining unclassified, due to the absence of one or more components in the reference list. This can result in the classification algorithm being unable to identify a mineral phase, or misidentifying a specific phase.

Another problem related to the size of the spectra library is that the accuracy and speed of spectra deconvolution is negatively impacted by chemically similar reference spectra. For some points on the sample, the electron beam interrogation volume comprises multiple minerals, and will produce a convoluted spectrum, that is, a mixture of two or more spectra overlaid upon each other. In the prior art, deconvolution is performed without any assumptions as to the possible composition of the mixture. A combination of any two or more spectra from the reference list is considered possible, and all such possible combinations are compared with the experimentally obtained spectrum to determine the best match. As a spectral reference list grows, the probability of misclassification increases there are more possibilities for incorrect matching.

For example, FIG. 1 is an illustration of a mineral distribution image 100 taken from a sample. The image can be generated by scanning the sample with a high energy beam, and measuring the energy distribution of x-rays emitted from the sample as a function of scan position. On a per pixel basis, these energy distributions can be fitted and/or compared to a known reference catalog 102 of energy distributions obtained from pure elements and pure minerals in order to identify the minerals in the sample at each scanned position. Different colors can be assigned to different minerals in the catalog 102, and an image of the spatial mineral distribution in the sample can be generated by plotting the colors of identified minerals as a function of scanned positions. Techniques for identifying minerals based on a catalog of elemental x-ray spectra are disclosed, for example, in AU2009212187 for "Method and System for Spectrum Data Analysis" of Corbett et al., U.S. Pat. No. 8,937,282 for "Mineral Identification Using Mineral Definition Including Variability" of Owen et al., and U.S. patent application Ser. No. 14/073,523, filed Nov. 6, 2013, for "Sub-pixel Analysis and Display of Fine Grained Mineral Samples" of Owen et al., all of which are herein incorporated by reference in their entirety. The energy spectrum collected from each pixel is compared to the spectra of pure elements and pure minerals in catalog 102 resulting in an undesirably long computing time. Additionally, comparing the sample on a per pixel basis to catalog 102 increases the chance for misidentification. As an example, area 104 shows a clay region made up of a convoluted mixture of minerals that are difficult to verify because the spectra of the convoluted mixture of elements can be misidentified as a material or mixture with a similar spectra. Area 106 shows a region incorrectly identified as magnesite (light blue), rather than the correct identification of magnesium-rich dolomite.

SUMMARY OF THE INVENTION

An object of the disclosure, therefore, is to provide an improved mineral analysis.

The composition of various points in a sample is analyzed using a two-step process. In the first step, data from the sample in analyzed to determine material present in the sample. The material identified in the first step is used to compose a sample-specific material library. In the second step, the sample-specific library is used to identify combinations of materials at points in the sample.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the scope of the invention as set forth in the appended claims.

BRIEF DESCRIPTION OF THE DRAWINGS

FIG. 5 is a table showing the average accuracy of identification on a series of synthetic mineral samples, comparing the prior art and the proposed two-step classification;

DETAILED DESCRIPTION OF PREFERRED EMBODIMENTS

Figure 1:
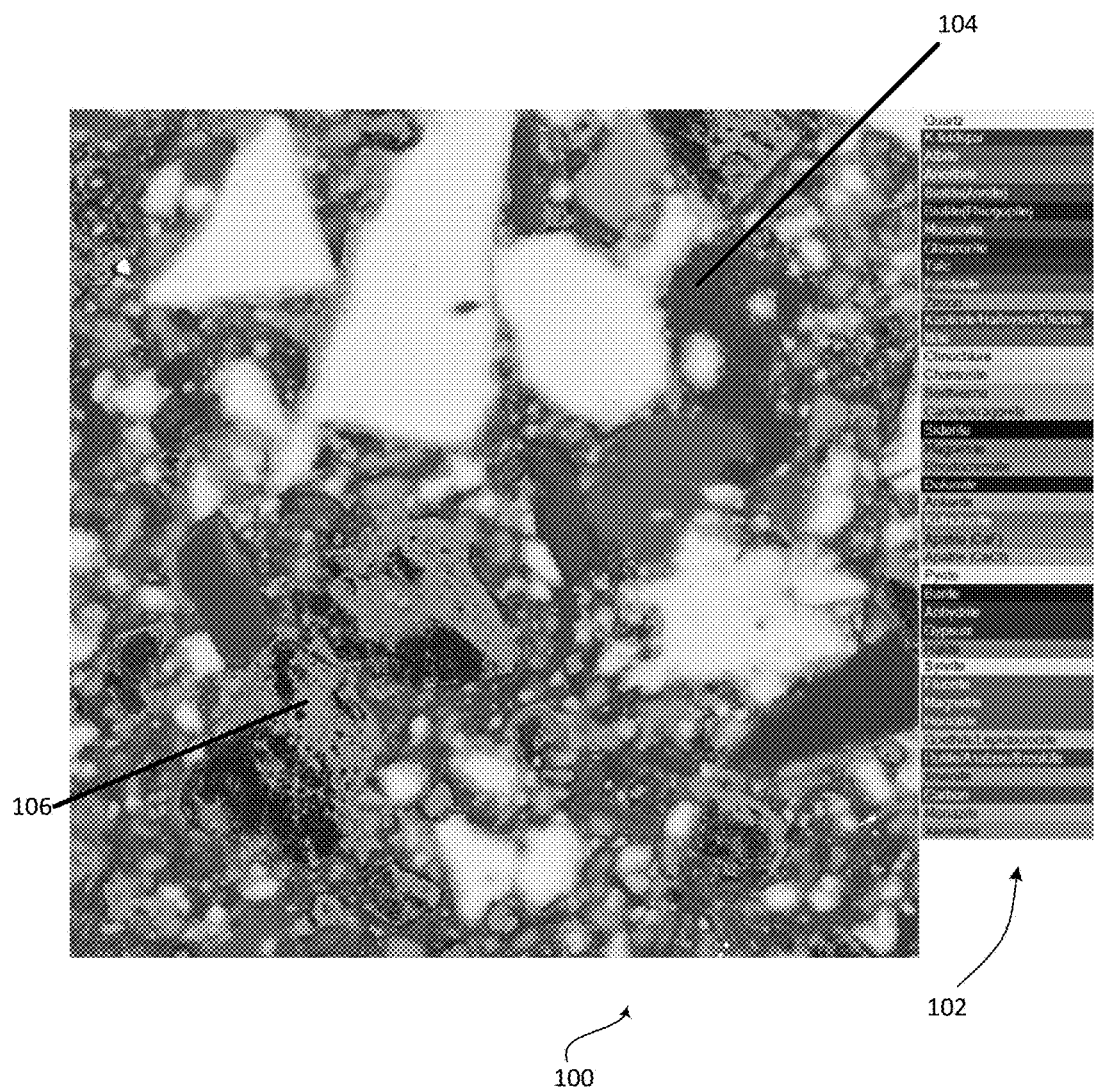
FIG. 1 is an enlarged view of a sample containing composite material showing minerals that were misidentified when classified using a prior art process using a reference list of shale minerals, performing purely mathematical selection of the minerals at each pixel without any context from the sample.

Embodiments of the present invention provide a method for identifying the mineral phases present in a sample. The composition at each point is determined from a spectrum or other characteristic measurement obtained at each point on the sample. The points typically contain multiple mineral phases, and so the spectrum or other measurement is typically a composite spectrum or measurement characteristic of multiple elements. Determining the material present in the sample is referred to as "material classification." The invention is not limited to any particular type of analysis or spectrum. It may be useful in various analysis applications in which the sample is composed of multiple components, particularly when the smallest portion of the sample from which information is derived, such as a beam interaction volume, includes multiple materials, and the analysis thus requires deconvolving the measured data into multiple components. The techniques described herein may be useful, for example, for analysis techniques using x-ray spectra, electron backscatter diffraction analysis, electron energy loss spectroscopy (EELS), light spectroscopy, and Raman spectroscopy. Typically EELS is performed with a focused beam and the interaction volume will be very small, but one can defocus the electron beam and the combined EELS spectrum will come from a larger area of the specimen. In such a case, each pixel of the composition map corresponds to a combined spectrum from the interaction volume of the defocused beam. Similarly, one can scan an area and collecting the EELS (and/or EDS) spectrum per pixel. In post-processing the user can then combine the spectra from multiple pixels to reduce analysis time. Integrated EELS spectra can be formed for groups of pixels in scanned area. The groups of pixels are treated like individual measurement points that may contain pure materials or combinations of materials, and the analysis is performed as described below. The pre-classification step can be performed on the combined spectra from the groups of pixels, and then the spectra of the groups of pixels can be deconvoluted to determine the combination of materials at individual points that make up the individual pixel group.

In one embodiment, a measured x-ray spectrum is obtained using a scanning electron microscope (SEM) to perform an energy-dispersive spectra (EDS) classification. Preferably, the SEM instrument will have a stored library containing high quality spectra for pure minerals and pure elements to serve as a reference spectral catalog against which measured spectra are compared. In some embodiments, measurements are recorded at multiple points and a materials list is compiled from points in which the interaction volume is dominated by a single material. This materials list is then used to determine combinations of materials at points in which the interaction volume contains multiple materials.

Embodiments of the invention facilitate an automated approach to mineral classification by automatically limiting the number of reference spectra used in material classification. Embodiments can increase the accuracy of mineral identification; while at the same time significantly reducing the computing time. Some embodiments allow supporting a global mineral reference library of more than 100 minerals which at present is not practical in any existing spectral analysis engine. In other embodiments, the global mineral reference library may have more than 70 spectra, more than 50 spectra, or more than 30 spectra. Using prior art methods, it was impractical to use more than about 30 spectra in the reference library because of the exponential increase in processing time with the number of spectra.

Some methods use a sample-specific reference spectral list or library. These methods provide a sequential approach to SEM-EDS automated mineralogy classification by performing two or more material classification analyses. Applicants have realized that in a given aggregate sample, that is, a sample composed of multiple mineral phases, the individual mineral constituents are likely to be at least occasionally present as a pure phase somewhere in the sample area under study. This results, at least in part, because certain minerals must physically fulfill size requirements and can't be present in sub-micron quantities only.

Such pure phase regions are larger than the physical volume of material from which the signal is obtained. For example, it is likely that there is a pure phase region of a mineral that is larger than the x-ray interaction volume excited by the electron beam used in EDS analysis. A spectrum obtained from such a pure phase region is representative of the pure material. "Pure material" is used herein to mean "dominant material," that is, a material that is readily recognized with high confidence from a measured spectrum, even if the measured spectrum also includes additional materials. The pre-classification step rapidly identifies materials that are present in the sample, thereby reducing the number of materials that need to be used in the compositional analysis. During the classification step, points of the sample that had been identified as "pure materials" are analyzed to determine what other materials are present at that point. A first, pre-classification step can be limited to identifying the dominant minerals in the sample. Given the large number of acquisition points (generally >100,000) it can be assumed that these pure phases will be encountered in a first-pass dominant-mineral-only pre-classification step. The dominant minerals are aggregated to form a sample-specific reference library used in a second, mineral classification step. In addition, a number of other minerals may be added, based on the knowledge of the specific sample. For example, these additional minerals can be commonly occurring trace minerals such as zircon, which are commonly form tiny mineral grains and may not be present in pure form because their physical size is always smaller than the measurement volume. The pre-classification step obviates the need to use a larger, non-sample specific mineral library.

The pre-classification step limits the application of computationally intensive spectra deconvolution algorithms to a subset of sample-specific spectra that have passed the dominant mineral criteria. Dominant mineral criteria can be designed by defining a spectral match threshold for matching the measured (raw) spectrum with a single known reference spectrum. Additional criteria can be defined, such as a minimum number of pixels (or area percent) for a given match. This approach can be fine-tuned by entering separate values depending on the nature of minerals, i.e., not to exclude trace minerals.

The pre-classification step results in a significantly reduced, sample-specific set of reference spectra that occur within the measured sample in pure enough form at a given minimum quantity. The sample-specific set of reference spectra will typically include spectra of about ten to twenty minerals. The number of reference spectra in the sample-specific set is typically relatively independent of the number of the number of spectra used in the pre-classification step. Thus, the number of mineral spectra in the sample-specific reference set can be reduced to less than ½ the number of spectra used in the pre-classification step to identify pure materials. In other embodiments, the sample specific reference set may include less than ¾, less than ⅔, less, than ½, less than ⅓, less than ¼, or less than ⅕ of the spectra used in the first analysis to determine the pure materials present in the sample. The following complex classification stages involving deconvolution of multiple constituents within measured spectra is based on this sample-relevant subset, with the addition of any other materials suspected to be present.

In the pre-classification step, the sample block is typically divided into rectangular tiles, each tile having dimensions such that the tile can be scanned by the electron beam without moving the sample. Each tile is divided up into dwell points that correspond to pixels on the compositional map. Each tile is scanned by the electron beam while collecting x-rays at each dwell point in the tile, and the composition of each dwell point is analyzed for pure materials. The pure materials are added to the sample-specific reference spectra library for the final classification.

In some embodiments, the compositional analysis can be performed concurrently with the electron beam scan. The computation time can be similar to the data acquisition time, typically about 2 ms per pixel. Depending on the homogeneity of the sample, a point is eventually reached during the pre-classification analysis where this library does not change, triggering the full classification. This process repeats for all tiles, and the list of minerals to use for analysis will converge during the measurement process. Common trace minerals are included in a priori, to further limit the need to reclassify the full sample at a late stage in the measurement. As a further refinement, a reclassification of a previously measured frame reuses the results computed for that frame from an earlier pass, resulting in no increase in overall computation time.

As a result, both speed and accuracy of spectral matching are increased allowing significant increase of the reference spectra library towards developing a single library that can be globally applied to a wide range of samples.

Figure 2:
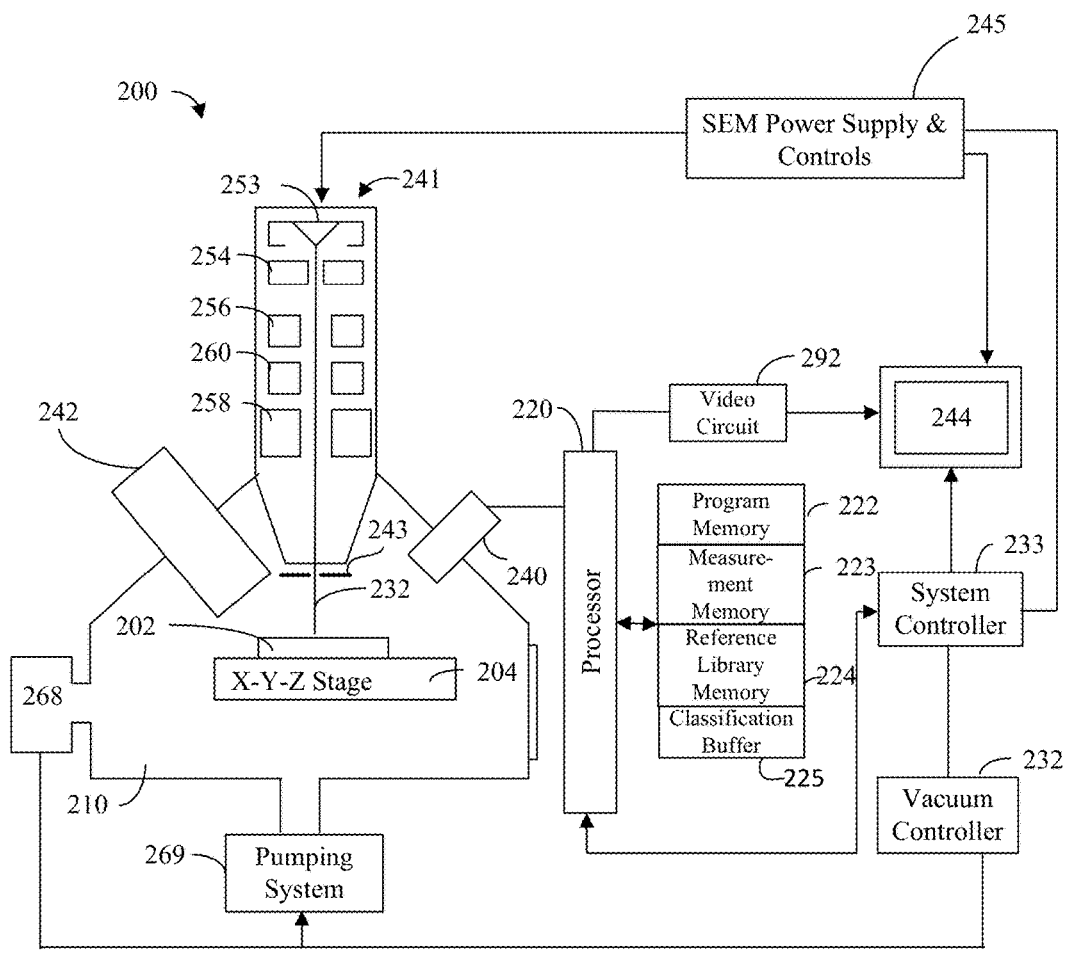
FIG. 2 shows a scanning electron beam with an X-ray detector suitable for analyzing standards according to preferred embodiments of the invention.

FIG. 2 is an illustration of a mineral identification and analysis system 200. The mineral identification system 200 includes a scanning electron beam system 241, an x-ray detector 240, a secondary electron detector 242, and a backscatter electron detector 243. An electron beam 232 emitted from a cathode 253 is accelerated toward an anode 254. Electron beam 232 is subsequently focused to a fine spot by means of a condensing lens 256 and an objective lens 258, and can be deflected across a sample 202 by means of a deflection coil 260 to perform a two-dimensional raster scan of the sample. The condensing lens 256, objective lens 258, and deflection coil 260 are supplied current by a power supply 245 operated under the control of a system controller 233. The sample 202 is preferably mounted on a movable X-Y stage 204 within a vacuum chamber 210. The vacuum chamber 210 is evacuated to high vacuum by a mechanical pumping system 269 and an ion pump 268 operated under the control of vacuum controller 232.

When the electron beam 232 strikes the sample 202, several forms of radiation are emitted, including backscattered electrons from the electron beam 232, secondary electrons produced by interactions between the electron beam 232 and the sample 202, and x-rays produced by interactions between the electron beam 232 and the sample that are characteristic of the elements in the sample 202. The secondary electrons produced by interaction between electron beam 232 and sample 202 are detected by a secondary electron detector 242, which outputs a signal indicative of the flux or intensity of secondary electrons. This signal is received by processor 220 through a connection (not shown) and processed by a video circuit 292 to produce an image of the work piece. The x-rays emitted from the sample 202 are detected by x-ray detector 240, which preferably outputs a signal indicative of the energy of the detected x-rays. To that end, x-ray detector 240 is preferably an energy dispersive detector such as a silicon drift detector. The output signal of x-ray detector 240 can be amplified and received by processor 220. The electrons are detected by an electron detector 242, such as a scintillator-photomultiplier detector, known as an Everhart-Thornley detector, a PIN solid state detector, or any other suitable detector.

Processor 220 can be programmed to store, for each scanned pixel, a count of the number of electrons detected, a count of the number of x-rays detected, and a histogram counting the number of x-rays detected in each of a plurality of energy bins over some energy range. Typically, the energy range is on the order of 0-10 kiloelectron volts (keV), and is subdivided into energy bins of 10-20 eV, for a total of 500 to 1000 energy bins or channels per pixel.

System 200 also includes a display 244 for displaying images and the results of the mineral analysis, a program memory 222 for storing executable computer program code to program the processor 220, and a measurement memory 223 for storing measured data, such as per-pixel BSE counts, x-ray counts, and x-ray emission spectra recorded from sample 202, and a reference data memory 224 for storing library of standardized elemental or mineral x-ray emission spectra, and a classification buffer for storing information during the classification process. Program memory 222 can include computer storage media in the form of removable and/or non-removable, volatile and/or nonvolatile memory and can provide storage of computer-readable instructions, data structures, program modules and other data. Generally, the processor 220 is programmed by means of instructions stored in the various computer-readable storage media. Programs and operating systems are typically distributed, for example, by downloading over a network, on a solid-state memory device or on CD-ROMs. From there, they are installed or loaded into the secondary memory of a computer. At execution, they are loaded at least partially into the computer's primary electronic memory. The invention described herein includes these and other various types of computer-readable storage media when such media contain instructions or programs for implementing the steps described above in conjunction with a microprocessor or other data processor. The invention also includes the computer itself (not shown) when programmed according to the methods and techniques described herein.

While the embodiment shown uses a scanning electron microscope to generate x-rays from sample 202, other embodiments could employ a transmission electron microscope or a scanning transmission electron microscope. An x-ray fluorescence system could also be used to generate x-rays from sample 202. In other embodiments, different forms of characteristic radiation emitted from the sample, such as gamma rays, may be detected.

Figure 3:
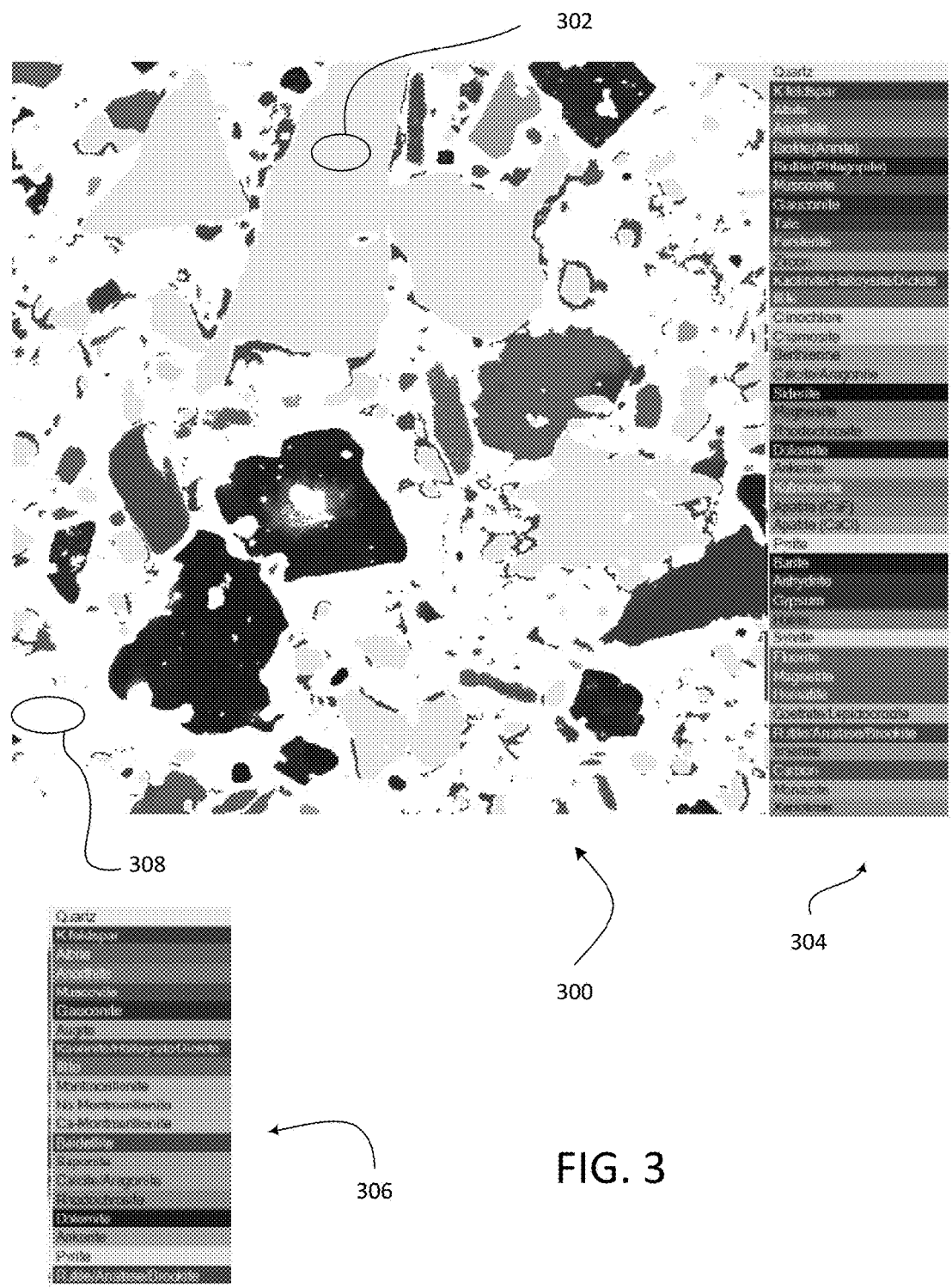
FIG. 3 is an enlarged view of a sample containing composite material showing pure minerals and a reference list of all minerals contained in the mineral database.

FIG. 3 is an illustration of the same sample shown in FIG. 1 showing a first mineral distribution image 300 taken in accordance with an embodiment of the invention. Image 300 can be generated by performing a scan of the sample with a high energy beam, such as between 5 keV and 30 keV, and measuring the energy distribution of x-rays emitted from the sample as a function of scan position. The energy distribution of each scanned pixel from the sample is fitted and/or compared to a full reference catalog 304 of energy distributions of pure elements and pure minerals. However, only those pixels having a spectrum matching a pure element or pure mineral are identified and recorded into the computer memory to form a sample-specific reference library 306 containing only those pure elements or minerals that are present in the sample.

In some embodiments, an image of the spatial mineral distribution of only the pure minerals or pure elements may be generated by assigning different colors to different pure elements or minerals in reference library 306. The spectra of pixels collected from the scan are compared to the spectra of pure elements and/or pure minerals in reference catalog 304 and only the spectra having a qualified match are selected as a pure element and/or pure mineral that form the reference library 306. Any pixels that do not meet the criteria of a pure element or pure mineral are disregarded. For example, the spectra of pixels contained in area 302 are compared to the spectra in reference catalog 304 and are identified as a pure mineral. This data is then stored in the computer memory to form a reference library 306. The spectra of pixels contained in area 308 do not match the pure mineral or pure element criteria and are not identified in the first analysis.

Figure 4:
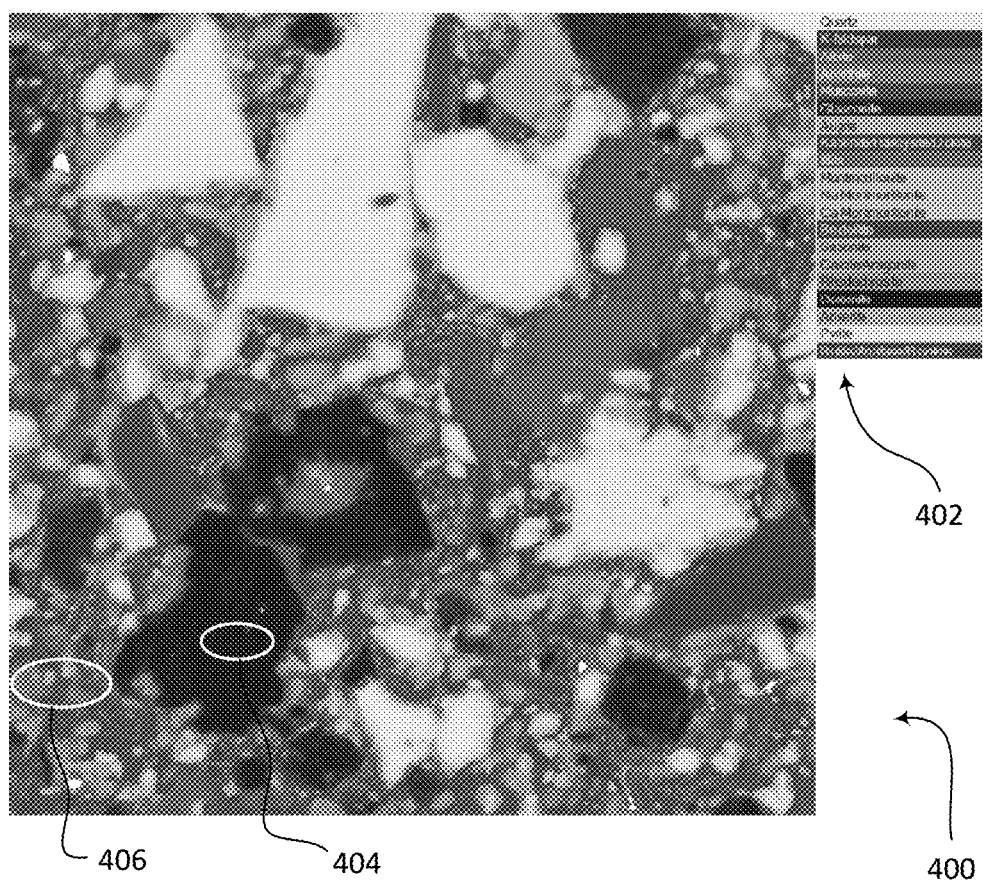
FIG. 4 is an enlarged view of the sample shown in FIG. 3 showing minerals contained in the sample as determined by reanalyzing the sample using the minerals found within FIG. 3.

A second analysis of the spectra obtained from the sample is then performed. The energy distribution of all pixels are fitted and/or compared to reference library 306, and deconvolution is attempted to identify areas of the sample containing a mixture of two or more minerals identified in the first analysis. In some embodiments, an image of the spatial mineral distribution of the sample can be generated. This can best be seen in FIG. 4, showing an illustration 400 of the mineral distribution of the sample generated after the second analysis. Since the complete reference library 402 is much shorter than the full catalog of pure elements and pure minerals used for the first analysis, the result is a material classification that is generated in a much shorter time and with higher accuracy.

FIG. 5 is a table 500 with results from an EDS analysis on a plurality of samples using both prior art material identification methods and material identification methods disclosed in embodiments of this invention. The samples consist of known ratios of synthetic mineral mixtures specifically chosen to be difficult to analyze due to similar chemistry. For example, it can be seen that the identification of mixture 113-rectorite-illite-montmorillinite had an accuracy of 31.75% with the prior art approach but was improved to 53.71% using methods disclosed in embodiments of the present invention.

Figure 6:
FIG. 6 is a graph showing the improved accuracy of back-calculated bulk elemental assay on a series of real shale samples with known elemental data, comparing the prior art and the proposed two-step classification.

FIG. 6 is a table 600 with results from an EDS analysis on a plurality of samples using both prior art material identification methods and material identification methods disclosed in embodiments of this invention. The samples came from the Vaca Muerta shale field and analysis was performed with existing analytical techniques to obtain bulk elemental data. They were also analyzed using the proposed approach to obtain bulk mineral data for each sample, and a conversion was performed from minerals to elements using chemical lookup tables to compute bulk elemental data. It can be seen that the identification of VacaMuerta_03 had an accuracy of 81.53% with the prior art approach but was improved to 87.41 using methods disclosed in embodiments of the present invention.

Figure 7:
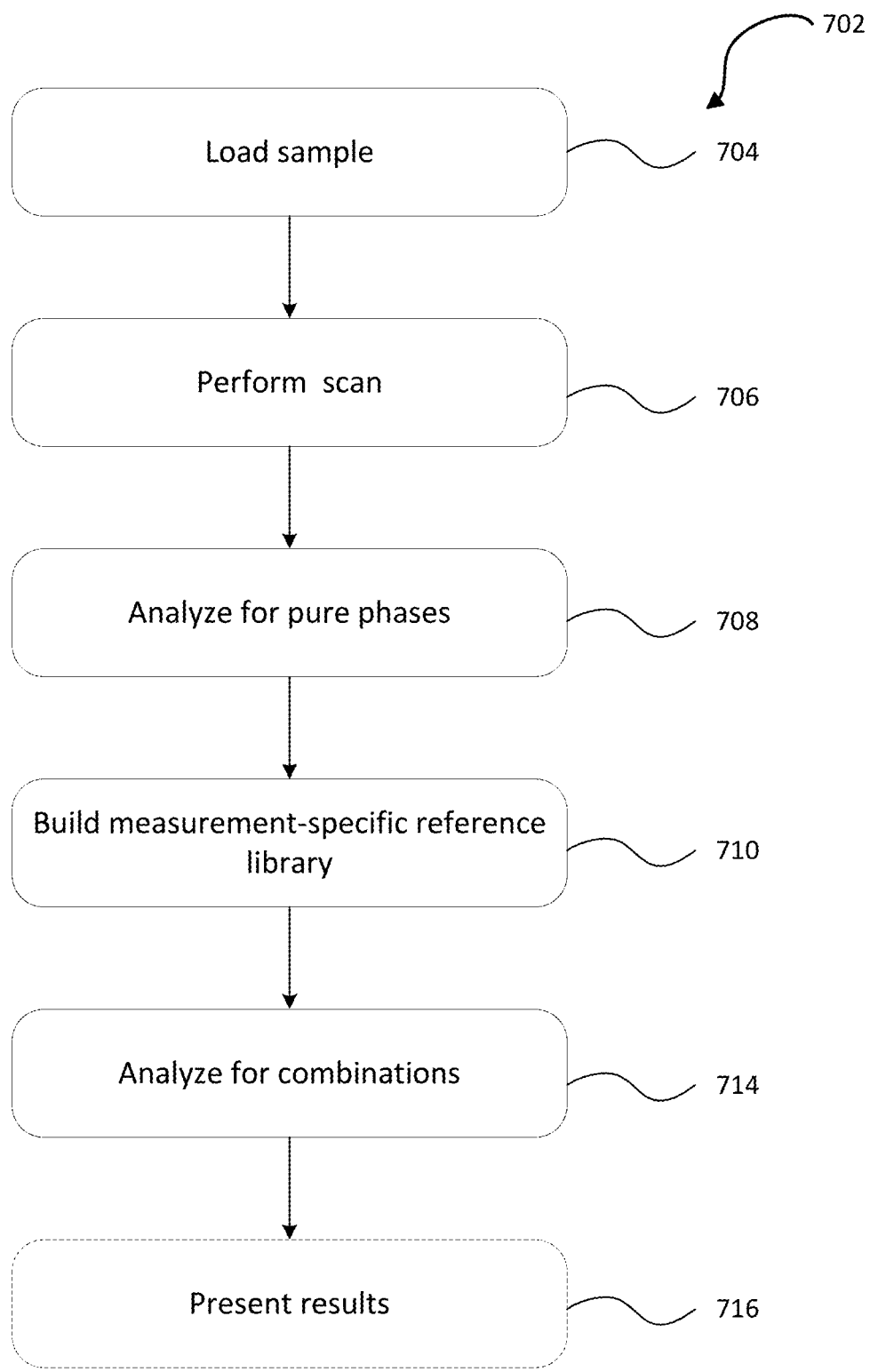
FIG. 7 is a flow chart of the steps of a method of mineral analysis.

FIG. 7 is a flow chart 702 showing the steps of an embodiment of the present invention. In step 704, a sample is loaded into the system 200 shown in FIG. 2. In some embodiments, the sample may be a geological specimen including an aggregate material comprising multiple minerals. For example, the sample may be from a core extracted from a mine or from drill cuttings returned from a well. In step 706, a scan of multiple points of the sample is performed, and compositional data from the sample are collected. These compositional data result from detection of byproducts of interaction between the beam and the sample. Possible byproducts of interaction between the incident beam and the sample include, but are not limited to, X-ray emission, x-ray diffraction patterns, electron backscatter diffraction patterns, and light emissions. In some embodiments, compositional data are collected in the form of X-ray emission spectra. These data may be collected and stored for later processing, or alternatively processed concurrently with the scan, or both. In step 708, a first analysis is performed on the compositional data collected in step 706.

In some embodiments, the first analysis is performed by attempting to match the collected compositional data with a single reference spectrum from a reference library comprising a multiplicity of individual reference spectra. The matching step may use a best fit matching routine, such as a least square algorithm that characterizes the difference between the measured spectrum and a spectrum from the library to produce a difference metric. In some embodiments, a difference metric is determined to represent the difference between the measured spectrum and the spectra of each of the materials in the library. The unknown material is identified as the library material whose spectrum produces the smallest difference metric when compared with the measured spectrum, if the difference metric is below a predetermined value. If the difference metric is not below the predetermined value, then the system concludes that the measured point is not composed of a pure material from the library. In some embodiments, the first analysis is an analysis identifying pure phases in the sample. In some embodiments, the pure phases are individual minerals which comprise an aggregate geological sample. In some embodiments, pure phase identification is performed by setting a match accuracy threshold, and excluding those areas on the sample where the collected compositional data does not meet the threshold for pure phase identification.

It is assumed that areas of the sample which do not meet the match accuracy threshold represent areas of the sample which are comprised of a mixture of two or more pure phases. In addition, it is assumed that, with a large enough sample area and small enough beam spot size, any material present in the sample, whether present as a mixture or as a pure phase, will be present somewhere within the sample area as a pure phase.

In step 710, a sample-specific reference library is constructed using information gathered in step 708. The sample-specific reference library may comprise only those materials which were identified as being present in the sample as a pure phase in step 708. In other embodiments, other materials, such as materials expected to be found in trace amounts in the sample, may be added to the sample-specific reference library. It should be noted that the sample-specific reference library typically contains fewer materials than the reference catalog used for material identification in step 708.

In step 714, a final analysis is performed on the data collected in step 706. This final analysis may proceed with a method similar to that presented in step 708, but the final analysis attempts to match the compositional information with possible combinations of reference materials rather than attempting to match the measured data with a single reference material. In some embodiments, when attempting to match the data collected during step 712, the second analysis uses only the sample-specific reference library constructed in step 710, rather than the entire reference catalog, as may be used in step 708. Additional materials beyond those determined in step 708 may be added to the reference library if, for example, the user has reason to believe that such materials may be present.

The analysis of the points in step 714 using the sample-specific reference library can be performed using any analysis method, such as the analysis methods described in AU2009212187, "Method and System for Spectrum Data Analysis", or Corbett et al. The measured spectrum from each data point is decomposed into the spectra of known materials to determine which combination of known materials produces a spectrum that is closest to the measured spectrum at each point. The analysis can also include back scattered electron data and other data.

In optional step 716, the results may be presented to the system operator. In some embodiments of the disclosure, the areas of the sample identified in step 708 and step 714 may be combined into one representation of the composition of the sample. This representation may take the form of an image of the sample. In some embodiments, different materials may be represented by different colors on the output presented to the system operator.

Figure 8:
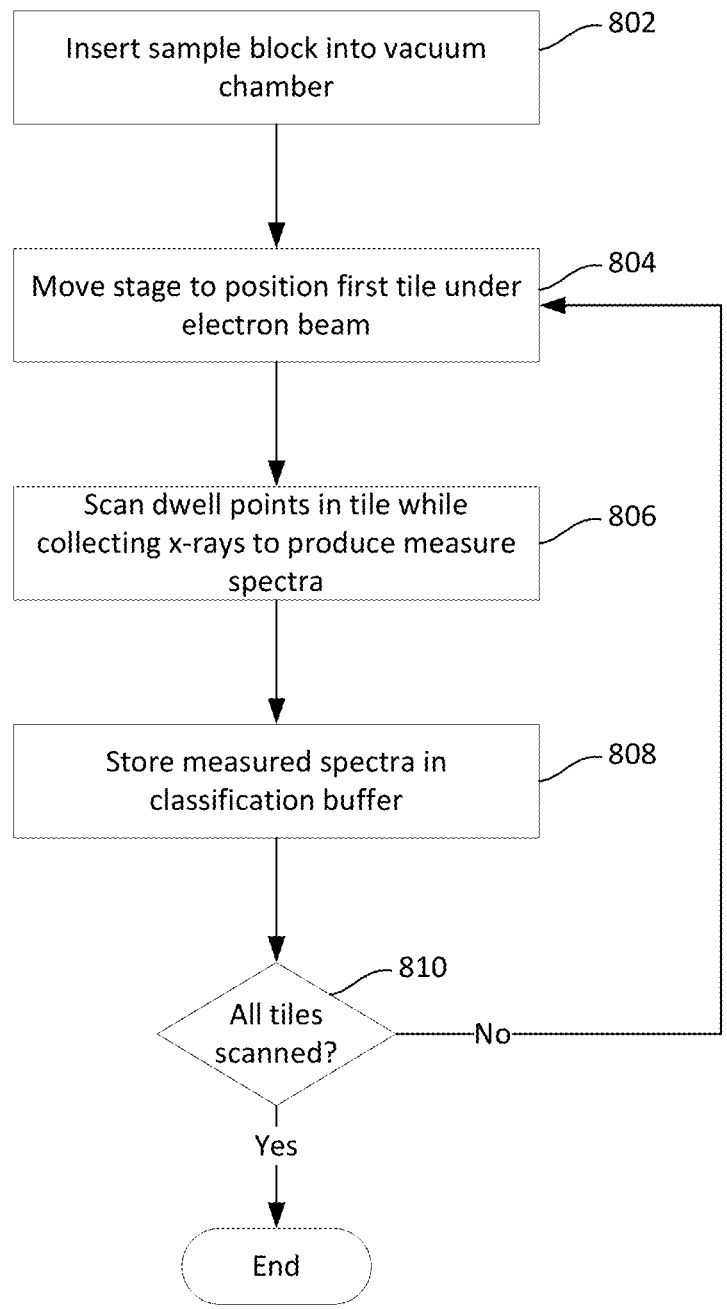
FIG. 8 is a flow chart showing a process for scanning a sample.
Figure 9:
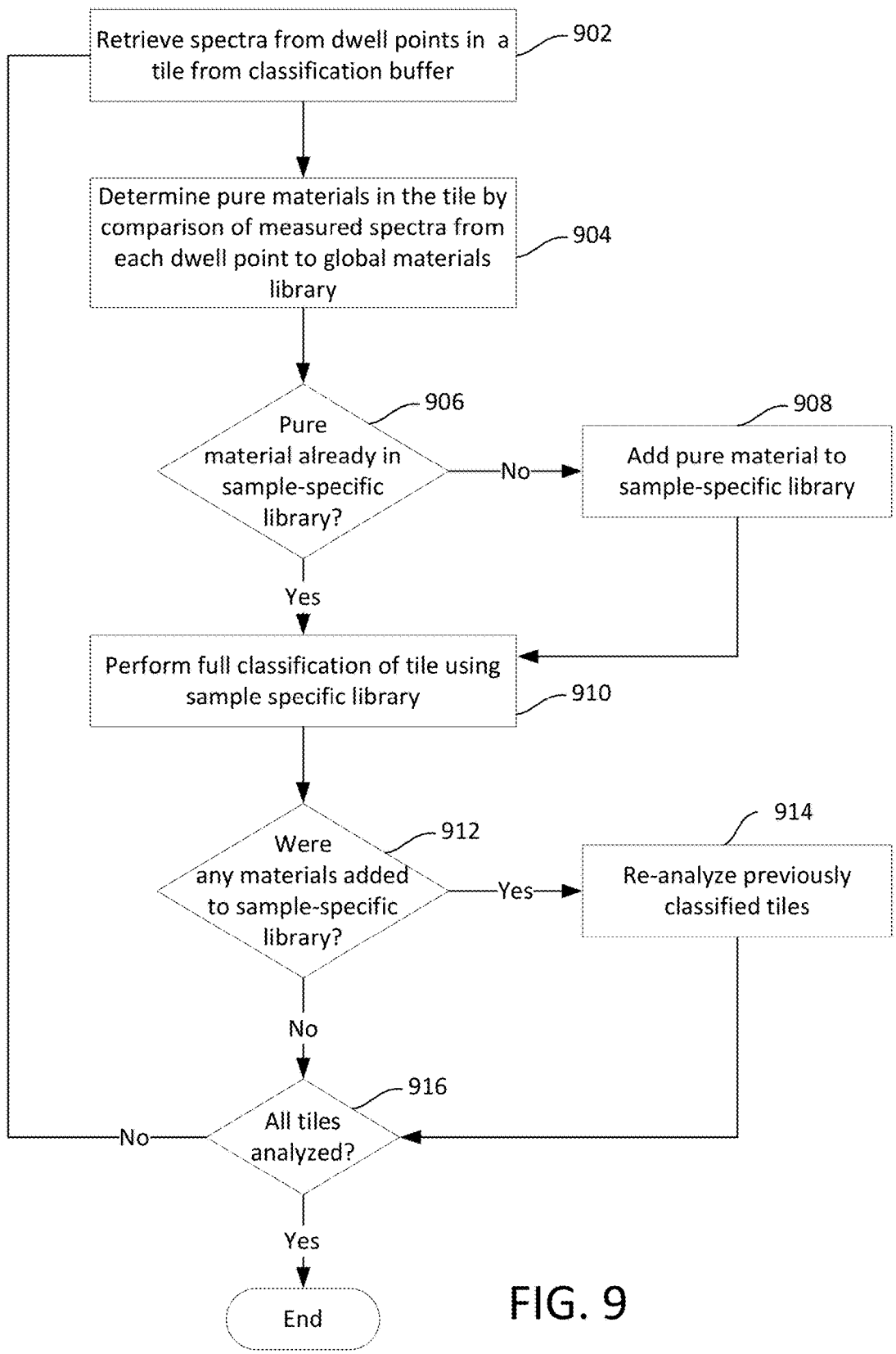
FIG. 9 is a flow chart showing steps of an on-line analysis.
Figure 10:
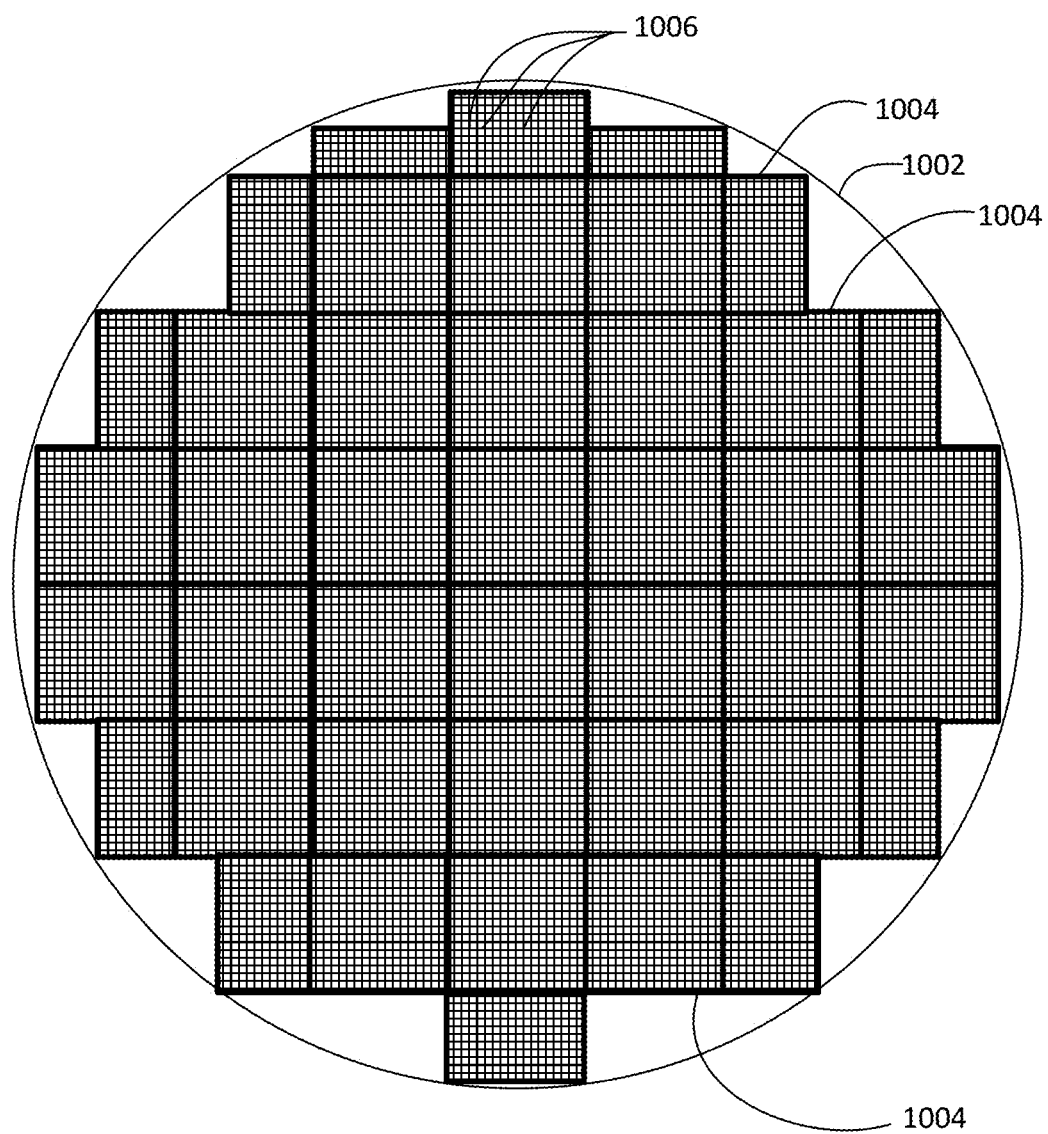
FIG. 10 shows the organization of a typical scan of a sample block.

FIGS. 8 and 9 are flow charts showing an on-line embodiment in which the analysis is preformed concurrently with the data collection. Because information is still being collected as the analysis is being performed, it will be necessary to re-analyze some data points as new information becomes available. FIG. 8 shows the data collection and FIG. 9 shows the data analysis.

FIG. 8 shows that in step 802, a sample block is inserted into a vacuum chamber. In step 804, the sample stage is moved so that the first tile is under the electron beam. In step 806, the electron beam scans points in the tile while an energy measuring x-ray detector collects x-rays to determine a measured spectrum. In step 808, the measured x-ray spectrum is stored in a classification buffer. Decision block 810 determines whether other tiles remain to be scanned, if so, the process repeats from step 804. If all tiles have been scanned, then the scanning is ended.

FIG. 9 shows the analysis steps of an embodiment. The steps of FIG. 9 can begin as soon as the first measurement data from step 808 of FIG. 8 is stored in the classification buffer. In step 902, the spectra from dwell points in a tile are retrieved from the classification buffer. In step 904, the spectrum of each dwell point is analyzed to determine whether the dwell point is composed of a pure material by comparing the measured spectrum from the dwell point to spectra in a global materials library. Decision block 906 determines whether or not the pure material identified in step 904 is already in the sample-specific library. If the material is not already in the library, it is added to the library in step 908. In step 910, the full classification of the dwell points in the tile is performed, using the sample-specific library of pure materials found in previous steps.

In decision block 912, it is determined whether any materials were added to the sample-specific library in step 908. If so, then all previously tiles are analyzed to determine whether or not the dwell points need to be reclassified using the new sample-specific library. Only the differences in the mineral lists are required for reclassification, and previous classification results are only overwritten if the new classification is better. The previous classification result is still valid if the deconvolution using the new minerals is not a closer match than the old combination. Decision block 916 determines whether all tiles have been analyzed. If not, the process continues with analyzing the next tile in step 902. If decision block 916 determines whether all tiles have been analyzed so, then the analysis of the sample is complete and the process is ended. While the method of claim 9 shows recalculating after each tile, in other embodiment, the recalculation can be performed whenever a new material is added to the sample-specific library.

The example provided above using energy dispersive x-ray analysis, the invention is useful for any analysis technique in which the combinations of materials present in a sample are determined by comparison with a library of material characteristics. It is particularly useful for analytical techniques that require spectral comparisons. The invention is not limited to x-ray analytical techniques. For example, it can be used for electron backscatter diffraction pattern analysis, in which there may be multiple crystal structures in the interaction volume that diffracts the electron beam. If there are multiple crystal structures under the interaction volume, then the result is a super-position of diffraction patterns. This technique would be applicable to selecting a small set of diffraction patterns from which to deconvolve and hence obtain a "mixed" result for that pixel.

Some embodiments of the invention provide a method of identifying materials in a sample, comprising the steps of:

collecting from multiple points on the sample measurement data providing information from which the composition of the sample at the multiple points can be determined;

analyzing the measurement data to identify materials present in a pure phase at any of the multiple points in the sample;

forming a sample-specific reference library containing materials identified as present in a pure phase at any of the multiple points in the sample; and analyzing the measurement data using the sample-specific library to determine the composition of the multiple points on the sample.

In some embodiments, analyzing the measurement data to identify materials present in a pure phase comprises comparing the measurement data to a global reference library containing spectra of known pure elements and/or minerals.

In some embodiments, the sample specific reference library comprises less than two thirds of the materials in the global reference library.

In some embodiments, at least a portion of the step of collecting from multiple points on the sample measurement data and at least a portion of the step of analyzing the measurement data to identify materials present in a pure phase are performed simultaneously.

In some embodiments, analyzing the measurement data using the sample-specific library to determine the composition of the multiple points on the sample includes re-analyzing the multiple points when additional materials are added to the sample-specific library.

In some embodiments, re-analyzing the multiple points comprises re-analyzing the material using only combinations including the material newly added to the sample-specific library.

In some embodiments, collecting from multiple points on the sample measurement data comprises directing an electron beam toward the multiple points on the sample and collecting an x-rays spectrum from each of the multiple points.

In some embodiments, the sample specific library contains x-ray spectra of pure materials.

In some embodiments, collecting from multiple points on the sample measurement data comprises collecting diffraction data.

In some embodiments, collecting from multiple points on the sample measurement data comprises collecting spectral data.

In some embodiments, collecting measurement data includes collecting x-ray data, electron backscatter diffraction data, electron energy loss data, or light data.

In some embodiments, analyzing the measurement data includes analyzing the data using x-ray spectroscopy, electron backscatter diffraction analysis, electron energy loss spectroscopy, light spectroscopy, or Raman spectroscopy In some embodiments, collecting measurement data includes collecting x-ray data, electron backscatter diffraction data, electron energy loss data, or light data.

In some embodiments, analyzing the measurement data includes analyzing the data using x-ray spectroscopy, electron backscatter diffraction analysis, electron energy loss spectroscopy, light spectroscopy, or Raman spectroscopy Some embodiments of the invention provide a method of identifying a material in a SEM system, comprising:

directing an electron beam toward multiple points on a sample;

collecting a measured x-ray spectrum from each of the multiple points on the sample;

analyzing the x-ray spectra from the multiple points on the sample to determine materials present in pure form at any of the multiple points on the sample; and analyzing the x-ray spectra from the multiple points on the sample to determine the composition of the sample at the multiple points.

In some embodiments, analyzing the x-ray spectra from the multiple points on the sample to determine materials present in pure form comprises comparing the x-ray spectra with reference spectra from a global reference library to form a sample-specific library of the materials present in pure form and in which analyzing the x-ray spectra from the multiple points on the sample to determine the composition of the sample at the multiple points includes analyzing the x-ray spectra from the multiple points using the sample-specific library.

In some embodiments, the global reference library includes more than fifty materials and in which the sample-specific reference library includes less than thirty materials.

Some embodiments of the invention provide a materials analysis system, comprising:

an electron beam focusing column;

an x-ray detector;

a control system for controlling the scanning electron microscope in accordance with operator instructions or stored instructions;

a computer memory in data communications with the scanning electron microscope and storing computer readable instructions for performing the steps of any of the methods described herein.

In some embodiments, the computer memory includes a global reference library and a sample specific library.

Although much of the previous description is directed at mineral samples from drill cores, the invention could be used to analyze samples of any suitable material. The terms "work piece," "sample," "substrate," and "specimen" are used interchangeably in this application unless otherwise indicated. Further, whenever the terms "automatic," "automated," or similar terms are used herein, those terms will be understood to include manual initiation of the automatic or automated process or step.

Although the present disclosure and its advantages have been described in detail, it should be understood that various changes, substitutions and alterations can be made herein without departing from the scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

In some embodiments, material identification is performed in a two-step process in which a first scan of the sample is performed to identify only the pixels whose spectra can be matched with a pure element or pure mineral from the reference catalog are classified in the first step. This data is stored to form a limited reference library containing only those pure elements and pure minerals that are in the sample. A second scan of the sample is then performed and the spectra not identified as a pure mineral or element is then measured against the reference library to identify those materials of mixed constituents. As a result of using a limited reference library identification of material is achieved in less time and with a higher degree of accuracy.

We claim:

1. A method of identifying materials in a sample, comprising:
    collecting from multiple points on the sample measurement data providing information from which the composition of the sample at the multiple points can be determined;
    analyzing the measurement data to identify materials present in a pure phase at any of the multiple points in the sample;
    forming a sample-specific reference library containing materials identified as present in a pure phase at any of the multiple points in the sample; and
    analyzing the measurement data using the sample-specific library to determine the composition of the multiple points on the sample.

2. The method of claim 1, wherein analyzing the measurement data to identify materials present in a pure phase comprises comparing the measurement data to a global reference library containing spectra of known pure elements and/or minerals.

3. The method of claim 2, wherein the sample specific reference library comprises less than two thirds of the materials in the global reference library.

4. The method of claim 1, wherein at least a portion of the step of collecting from multiple points on the sample measurement data and at least a portion of the step of analyzing the measurement data to identify materials present in a pure phase are performed simultaneously.

5. The method of claim 4 in which analyzing the measurement data using the sample-specific library to determine the composition of the multiple points on the sample includes re-analyzing the multiple points when additional materials are added to the sample-specific library.

6. The method of claim 5 in which re-analyzing the multiple points comprises re-analyzing the material using only combinations including the material newly added to the sample-specific library.

7. The method of claim 1, wherein collecting from multiple points on the sample measurement data comprises directing an electron beam toward the multiple points on the sample and collecting an x-rays spectrum from each of the multiple points.

8. The method of claim 7 in which the sample specific library contains x-ray spectra of pure materials.

9. The method of claim 1, wherein collecting from multiple points on the sample measurement data comprises collecting diffraction data.

10. The method of claim 1, wherein collecting from multiple points on the sample measurement data comprises collecting spectral data.

11. The method of claim 1, wherein collecting measurement data includes collecting x-ray data, electron backscatter diffraction data, electron energy loss data, or light data.

12. The method of claim 1, wherein analyzing the measurement data includes analyzing the data using x-ray spectroscopy, electron backscatter diffraction analysis, electron energy loss spectroscopy, light spectroscopy, or Raman spectroscopy.

13. The method of claim 1 in which:
    collecting from multiple points on the sample measurement data comprises collecting from multiple points on the sample x-ray spectral data;
    analyzing the measurement data to identify materials present in a pure phase at any of the multiple points in the sample comprises analyzing the x-ray spectral data to identify materials present in a pure phase at any of the multiple points in the sample; and
    analyzing the measurement data using the sample-specific library comprises analyzing the x-ray spectral data and the sample-specific library to determine the composition of the multiple points on the sample.

14. The method of claim 1 further comprising, before analyzing the measurement data using the sample-specific library, adding spectra of a trace mineral to the sample-specific library.

15. The method of claim 1 in which analyzing the measurement data using the sample-specific library to determine the composition of the multiple points on the sample comprises analyzing the same or a subset of the measurement data analyzed to identify materials present in a pure phase.

16. A method of identifying a material in a SEM system, comprising:
    directing an electron beam toward multiple points on a sample;
    collecting a measured x-ray spectrum from each of the multiple points on the sample;
    analyzing the x-ray spectra from the multiple points on the sample to determine materials present in pure form at any of the multiple points on the sample; and
    analyzing the x-ray spectra from the multiple points on the sample to determine the composition of the sample at the multiple points.

17. The method of claim 16 in which analyzing the x-ray spectra from the multiple points on the sample to determine materials present in pure form comprises comparing the x-ray spectra with reference spectra from a global reference library to form a sample-specific library of the materials present in pure form and in which analyzing the x-ray spectra from the multiple points on the sample to determine the composition of the sample at the multiple points includes analyzing the x-ray spectra from the multiple points using the sample-specific library.

18. The method of claim 17 in which the global reference library includes more than fifty materials and in which the sample-specific reference library includes less than thirty materials.

19. The method of claim 17 in which the sample-specific library includes reference spectra of about ten to twenty minerals, these minerals being selected from the group consisting of: albite, anatase, anhydrite, ankerite, annite, anorthite, apatite, aragonite, augite, barite, beidellite, berthierine, biotite, brookite, calcite, calcium montmorillonite, carbon, chamosite, chlorapatite, clinochlore, dickite, dolomite, feldspar, fluorapatite, fluorite, forsterite, glauconite, goethite, graphite, gypsum, halite, halloysite, hematite, illite, ilmenite, kaolinite, kutnohorite, lepidocrocite, magnesite, magnetite, monazite, montmorillonite, muscovite, orthoclase, phlogopite, potassium feldspar, pyrite, quartz, rectorite, rhodochrosite, rutile, saponite, siderite, sodium montmorillonite, sylvite, talc, xenotime, and zircon.

20. A materials analysis system, comprising:
    an electron beam focusing column;
    an x-ray detector;
    a control system for controlling the scanning electron microscope in accordance with operator instructions or stored instructions;
    a computer memory in data communications with the scanning electron microscope and storing computer readable instructions for performing the steps of claim 16.

21. The materials analysis system of claim 20 in which the computer memory includes a global reference library and a sample specific library.

\* \* \* \* \*